(12) United States Patent
Lehe et al.

(10) Patent No.: US 6,273,852 B1
(45) Date of Patent: Aug. 14, 2001

(54) SURGICAL INSTRUMENT AND METHOD FOR TREATING FEMALE URINARY INCONTINENCE

(75) Inventors: Jorn Lehe, Hamburg (DE); Chao-Chen Chen, Edison; Brian H. Luscombe, Warren, both of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/521,801

(22) Filed: Mar. 9, 2000

Related U.S. Application Data

(60) Provisional application No. 60/138,231, filed on Jun. 9, 1999.

(51) Int. Cl.[7] ....................................................... A61F 2/00

(52) U.S. Cl. ..................... 600/30; 128/DIG. 25; 600/37

(58) Field of Search ................................. 600/29, 30, 37; 60/119; 128/DIG. 25; 28/897, 898; 604/515

(56) References Cited

U.S. PATENT DOCUMENTS

| | | | |
|---|---|---|---|
| 5,112,344 | | 5/1992 | Petros . |
| 5,337,736 | * | 8/1994 | Reddy .................................. 600/217 |
| 5,362,294 | * | 11/1994 | Seitzinger .............................. 600/37 |
| 5,899,909 | * | 5/1999 | Claren et al. ......................... 606/119 |
| 5,934,283 | * | 8/1999 | Willem et al. ........................ 128/885 |
| 6,042,534 | * | 3/2000 | Gellman et al. ........................ 600/30 |

* cited by examiner

Primary Examiner—John P. Lacyk
(74) Attorney, Agent, or Firm—Verne E. Kreger, Jr.

(57) ABSTRACT

A is a surgical instrument and method for treating female urinary stress incontinence. The instrument includes a curved needle-like element defining in part a curved shaft having a distal end and a proximal end. The diameter of the needle decreases from the proximal end to the distal end, and the needle terminates in a blunt tip. A tape attaches to the needle for implanting into the lower abdomen of a female to provide support to the urethra. The tape may be made from synthetic and natural materials. The needle and tape may also be modified to allow the surgeon to attach and detach the tape during the surgical operation.

30 Claims, 23 Drawing Sheets

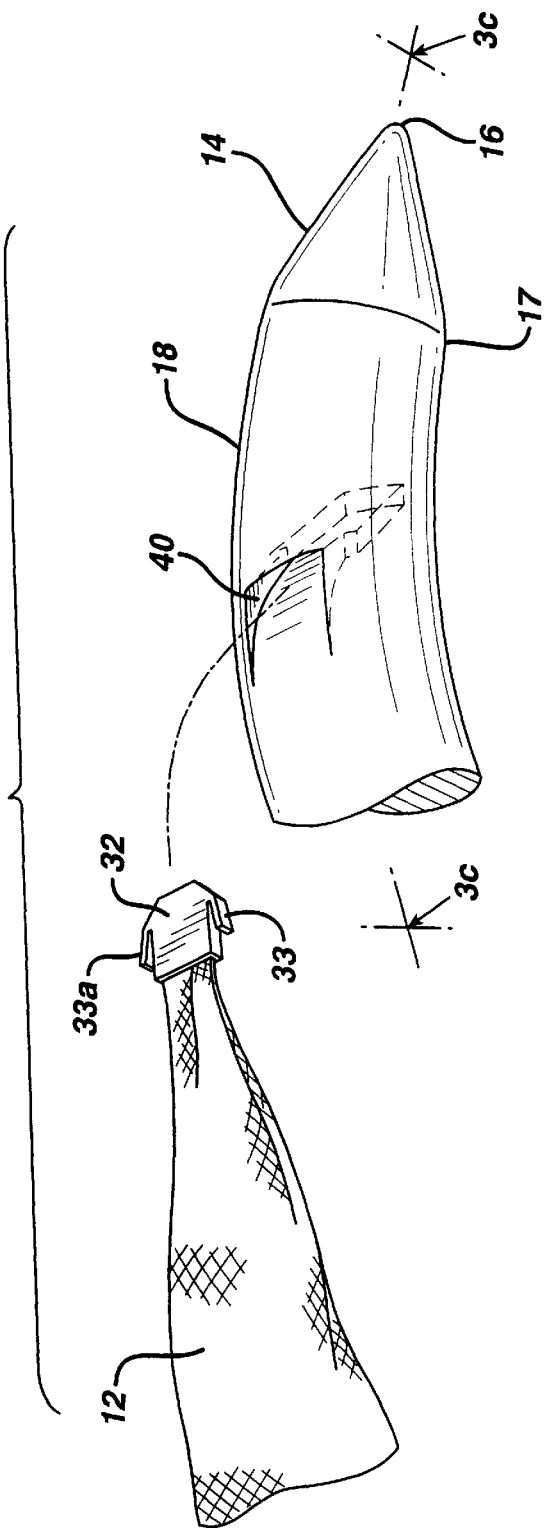
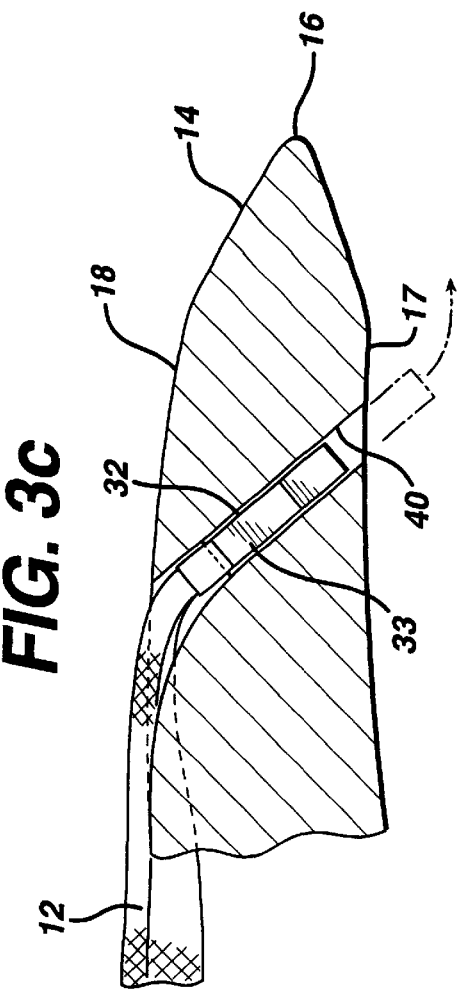

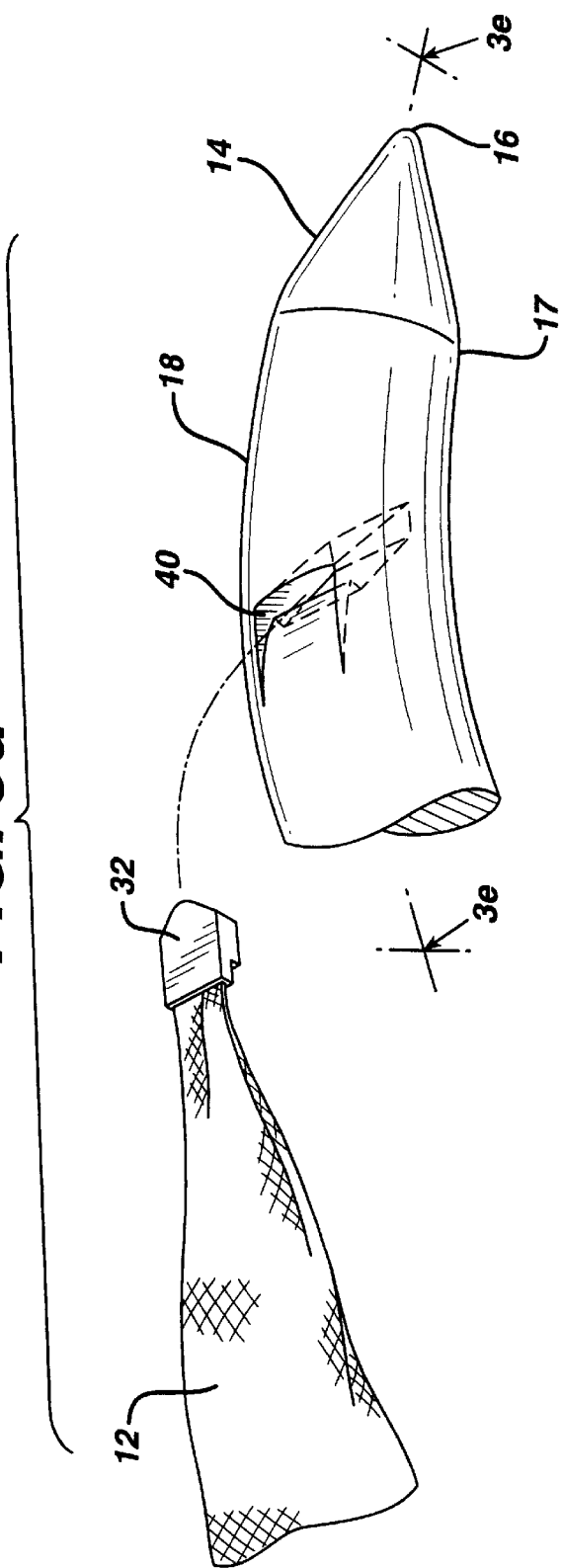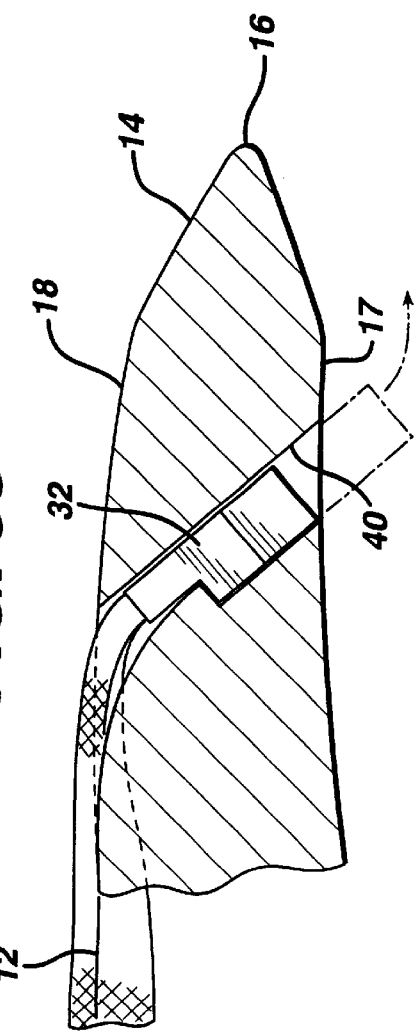

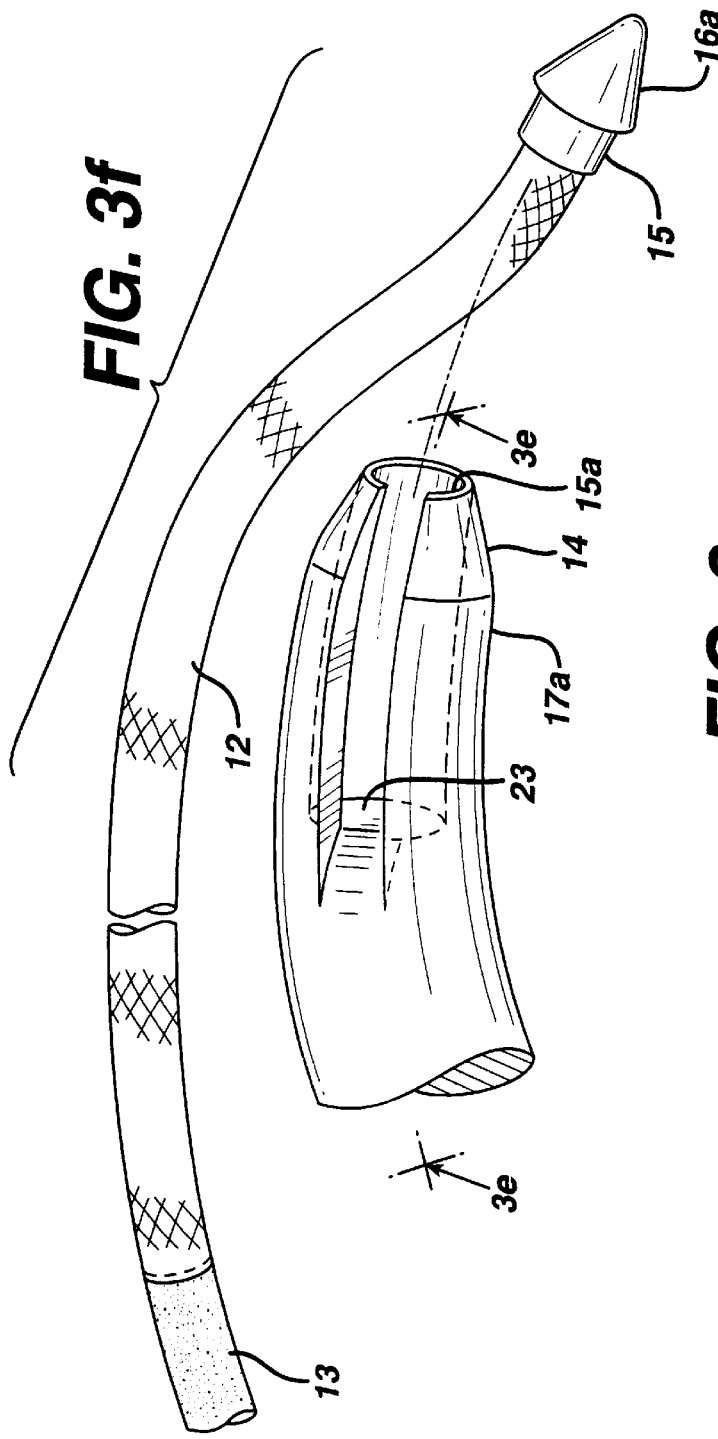
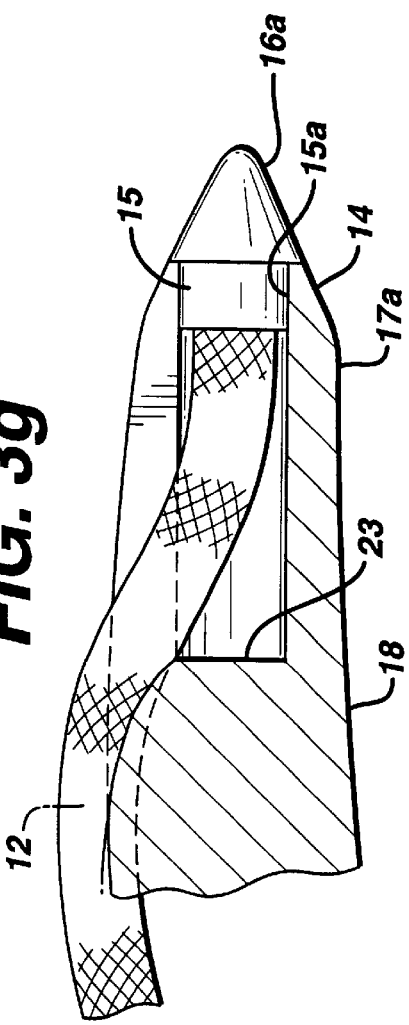
FIG. 3f
FIG. 3g

SURGICAL INSTRUMENT AND METHOD FOR TREATING FEMALE URINARY INCONTINENCE

CROSS REFERENCE TO RELATED APPLICATION

The present invention claims the benefit of earlier-filed U.S. provisional patent application, Ser. No. 60/138,231, filed on Jun. 9, 1999, which is hereby incorporated by reference in its entirety herein.

BACKGROUND OF THE INVENTION

The present invention relates generally to a surgical instrument and a method for treating female urinary incontinence and in particular to a conical needle for facilitating the perforation of different layers of tissue, with each tissue layer having a different resistance against perforation.

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise.

SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarrassing and unpredictable, many women with SUI avoid an active lifestyle, shying away from social situations.

U.S. Pat. No. 5,112,344 describes a method and apparatus for treating female incontinence. The surgical instrument for the application of a filamentary element into the body comprises a tubular shaft having a handle at one end and a flexible needle slidably receivable in the shaft and adapted at one end to receive a filamentary element. The method of treating female incontinence comprises looping a filamentary element between the wall of the vagina and the rectus abdominis sheath in the anterior wall of the abdomen whereby it passes to each side of the urethra, tightening the loop to bring the vaginal wall the urethra into the correct spatial relationship to the pubis allowing the development of scar tissue between the vaginal wall and the anterior wall of the abdomen pubic symphysis and removing the filamentary element.

U.S. Pat. No. 5,899,909 discloses a surgical instrument comprising a shank having a handle at one end and connecting means at the other end to receive, one at a time, two curved needle-like elements which are connected at one end to one end of a tape intended to be implanted into the body. In practice, the tape is passed into the body via the vagina first at one end and then at the other end at one side and the other, respectively, of the urethra to form a loop around the urethra, located between the urethra and vaginal wall. The tape is extended over the pubis and through the abdominal wall and is tightened. The tape ends are cut at the abdominal wall, and the tape is left implanted in the body.

Current needles for implanting tapes have a short conical tip and a curved body with a constant diameter. When the conical needle tip perforates a layer of human tissue having a high resistance against perforation (like fascia or muscle), the force required is high compared to the force required to perforate soft human tissue (like fat). To lower the maximum force required by the surgeon to penetrate fascia or muscle, the needle tip is pointed. After the conical tip passes through a tissue layer with a high perforation resistance, however, the force required to further pass the needle through the tissue suddenly drops close to zero. As an undesirable consequence then, the needle may penetrate through tissue faster than the surgeon intends, possibly causing the surgeon to lose control of the needle and risking the possibility of unintentionally perforating other body structures, such as, bone, organs or blood vessels, with the pointed needle tip.

It would be beneficial to provide a needle for use in implanting a mesh tape within a female body to prevent incontinence that has a design that provides for a more even resistance for perforating differing types of tissue.

It would also be beneficial to simplify the design of the surgical instrument to facilitate the loading of the tape onto a needle during the operation. In this manner, the instrument would be more receptive to various types of tapes, such as synthetic, cadaver tissue and engineered tissue.

SUMMARY OF THE INVENTION

The invention overcomes the deficiencies of the prior art and provides for an improved needle for use with an apparatus and a method for the treatment of female stress urinary incontinence. The invention provides a surgical instrument comprising a handle at one end and connecting means at the other end to receive, one at a time, two curved needle-like elements, each of which have a blunt tip and varying diameter. Each needle connects at one end to separate ends of a tape intended to be implanted within the body. In practice, a first end of the tape is passed, via one of the curved needles, into the body via the vagina at one side of the urethra. The needle and first end of the tape pass over the pubis and through the abdominal wall. The second needle element connects to the handle and to the second end of the tape. The needle and second end of the tape pass into the body via the vagina at the opposite site of the urethra from the first end of the tape thereby forming a loop or sling around the urethra with the tape. The second end of the tape is extended over the pubis and through the abdominal wall. The tape ends are cut at the abdominal wall, and the tape is left in the body.

The invention further provides for a single curved needle element having a blunt tip and varying diameter and further provides for a easy attachment means enabling the surgeon to connect both the first and second tape ends to the single needle to perform the above-stated procedure.

The invention still further provides for a tape comprising of a synthetic mesh in combination with a natural material whereby the natural material would reside below the urethra to eliminate potential erosion issues.

In one aspect the invention provides a needle element having a distal end and a proximal end. The diameter of the needle varies increasingly from the distal end to the proximal end. The distal end further defines a tip having a blunt end. The proximal end provides for a connecting means to the handle.

The object of the invention is to provide a surgical instrument that requires a reduced maximum force to pass the tape through body tissue.

A further object of the invention is to provide a needle that requires a more constant force to pass through body tissue.

An advantage of the invention is that it reduces the risk of perforating other body structures.

A further advantage of the invention is that it provides for a quick connecting means of the tape to the needle thus allowing for the use of non-synthetic tissue as the supporting element.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 3b–c is an enlarged view of the distal tip of the needle shown in FIG. 3a and a means for detachably connecting the tape to the needle;

FIGS. 3d–e is an enlarged view of the distal tip of the needle shown in FIG. 3a and an alternate means for detachably connecting the tape to the needle;

FIGS. 3f–g is an enlarged view of the distal tip of the needle shown in FIG. 3a and an alternate means for detachably connecting the tape to the needle;

DETAILED DESCRIPTION OF THE INVENTION

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the illustrative embodiments of the present invention for the The invention discloses an apparatus and method for treating SUI. A tape is passed through pelvic tissue and positioned underneath the urethra, creating a supportive sling. The tape provides a structure means for tissue ingrowth and thereby provides a newly created body tissue supporting means for the urethra. When pressure is exerted upon the lower abdomen, such as during a cough or sneeze, the tape provides support to the urethra, allowing it to keep its seal and prevent the unwanted discharge of urine.

Figure 1:
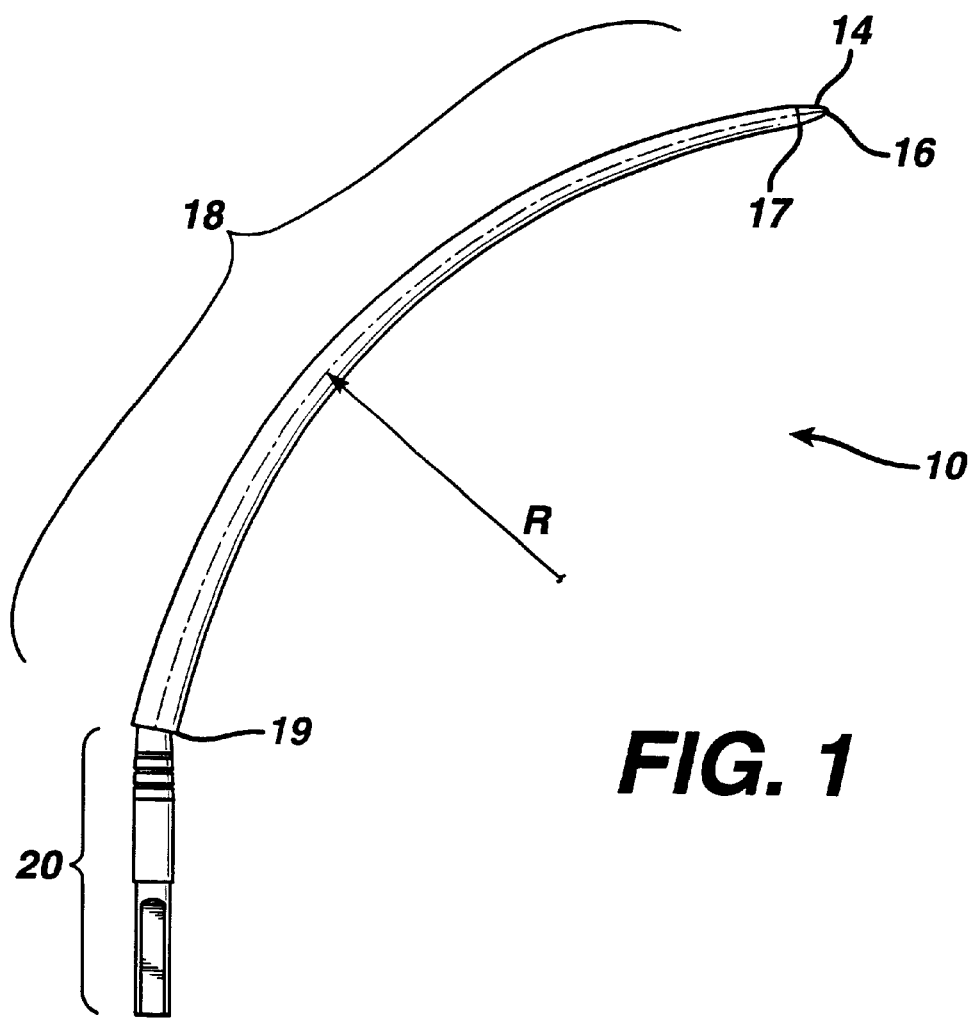
FIG. 1 is a side view of the needle in one embodiment thereof.

Referring to FIGS. 1 and 2, the surgical instrument comprises a needle-like element 10 that attaches to a mesh tape 12. Needle element 10 defines a certain radius R to perform the surgical procedure discussed herein. The distal end of needle element 10 terminates at a conical section 14 having a tip 16. Alternate configurations, such as a blade-like, arrow or burr tips are also possible. Preferably, tip 16 is blunt, wherein the tip 16 has a radius of about 0.6 millimeters. A blunt tip is preferred since it is less likely to stick in bone or penetrate bladder wall tissue or blood vessel wall tissue as will be appreciated from the method of implanting the tape as described below.

The proximal end of needle 10 terminates in an attachment segment 20 that is adapted to mate and lock into a handle 21 as disclosed in U.S. Pat. No. 5,899,909, previously incorporated herein by reference.

Disposed between tip 14 and segment 20 is a curved shaft segment 18 having a distal end 17 and a proximal end 19. The shape of shaft 18 extends substantially a quarter of a circle in order to follow substantially the profile of the pubis between the vagina and the abdominal wall. For the purposes of the method as will be discussed in more detail below, shaft 18 has a preferred radius R of about 106 millimeters. Further, the diameter of segment 18 transitions from a smaller diameter at distal end 17 to a larger diameter at proximal end 19. The minimum diameter of distal end 17 may be as small as 0.5 mm due to the minimal stresses at this point. The minimal diameter of proximal end 19 is about 4 mm. Preferably, the diameter at the proximal end is about 6 mm, and reduces in a continuous manner to a diameter of about 3 mm at the distal end 17. This design takes into account, that in the method to implant the tape 12, the bending stresses are lowest at distal end 17, while the bending stresses are highest at the proximal end 19. Stated differently, during the procedure, the inner bending moment at distal end 17 is negligible, while the inner bending moment at the proximal end 19 is substantial. The design is also beneficial in that the needle provides a tactile feedback to the surgeon as the needle passes through differing layers of tissue as opposed to a needle having a minimal diameter.

An unexpected result of needle 10 having a blunt tip 16 and a varying diameter shaft 18 is a reduced maximum force required to perforate a layer of tissue, such as fascia, muscle, fat and skin. Further, after needle tip 16 has passed through a tissue layer, the force required by the surgeon to continue the needle 10 through the tissue layer or subsequent tissue layers having lower resistances to perforation does not precipitously decrease as in the prior art. This is result of the shaft 18, having an increasing diameter from the distal end 17 to proximal end 19, having to continue to pass through the tissue, thereby requiring a more constant force from the surgeon.

Table 1 compares the force required to penetrate a fascia of a pig (lateral to the linea alba) between a needle of the prior art and a needle of the present invention. The prior art needle was characterized as having a 5 mm constant diameter and a needle tip having a radius of 0.2 mm. The needle of the current invention was characterized as having a varying diameter of 3 mm to 6 mm from the distal end to proximal end of curved shaft 18 and a needle tip having a radius of 0.6 mm. The fascia was placed into a testing device, and each needle perforated the fascia at an angle of 90° at a speed of 50 mm/min. Table 1 lists the maximum force needed to penetrate the test tissue:

TABLE 1

| Test No. | Prior Art Needle Maximum Force (N) | Needle of the present invention Maximum Force (N) |
| --- | --- | --- |
| 1 | 7.10 | 6.41 |
| 2 | 7.32 | 7.85 |
| 3 | 8.16 | 5.75 |
| 4 | 9.20 | 6.60 |
| 5 | 13.14 | 5.30 |
| Avg. Force (N) | 8.98 | 6.38 |
| s | 2.47 | 0.97 |

The test results indicate that the needle of the present invention reduces the penetration force by 29% over the prior art needle.

Needle 10 is preferably tubular with a circular cross section and is made from a material that is compatible with the human body. It is also preferred that needle 10 is made from a material that can be autoclaved to enable multiple surgical procedures of needle 10. Preferably, needle 10 is made from AISI 303 stainless steel. The surface of shaft 18 may be smooth, preferably polished, to facilitate penetration of the soft tissue. Alternatively, the surface of needle 10 may have a somewhat rougher surface. A rougher surface would result in slightly additional tissue trauma, which in turn stimulates fibroblast activity around the tape 12.

Needle 10 may be manufactured as a single, continuous unit, or alternatively, curved portion 18 may be manufactured separately from linear portion 20. In this manner the two pieces would attach using any conventional attaching means, such as, screwing, or other conventional means as is known to those skilled in the art.

Figure 2A:
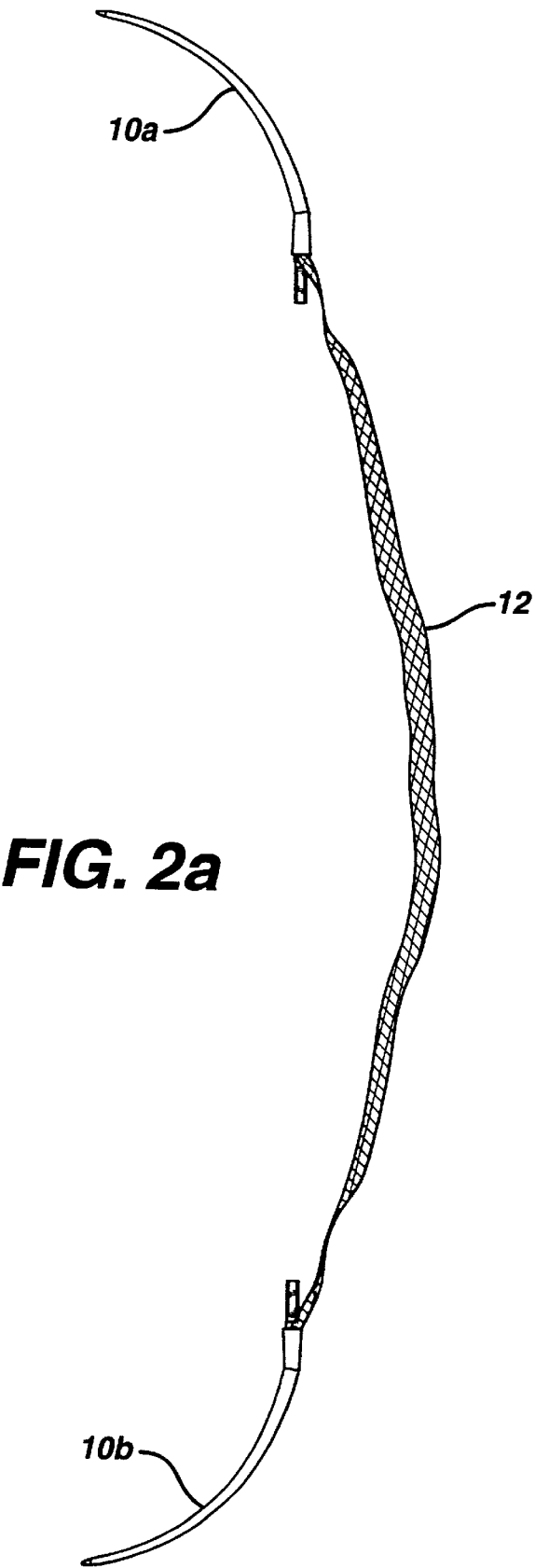
FIG. 2a is a side view of two needles and a tape interconnecting the needles.
Figure 2B:
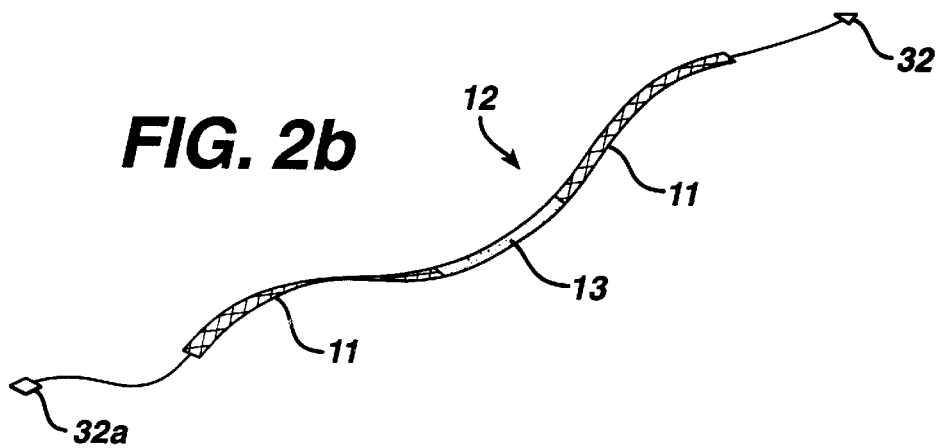
FIGS. 2b–d are alternate embodiments of the tape and connecting means between the tape and needle.
Figure 2C:
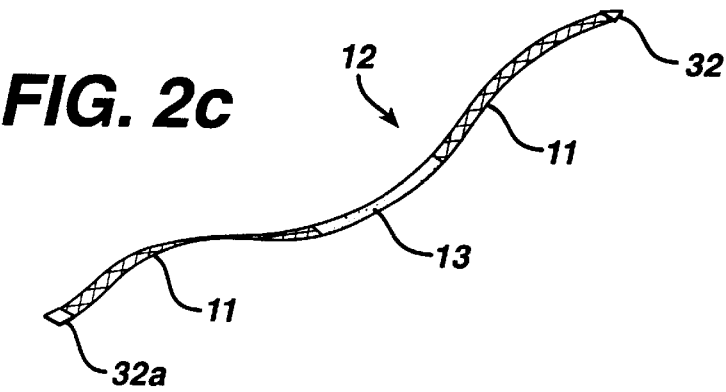
Figure 2D:
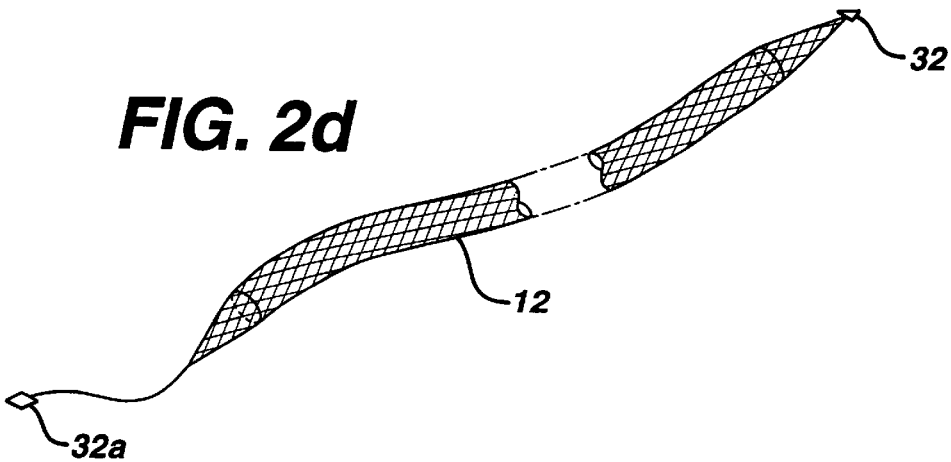

Referring to FIGS. 2a–d, tape 12 comprises any tissue-compatible synthetic material, or any natural material, including, but not limited to, autologous, allograft, xenograft, a tissue engineered matrix, or a combination thereof. An exemplary synthetic material is PROLENE® polypropylene mesh, a mesh having a thickness of 0.7 mm and openings of about 1 mm manufactured by Ethicon, Inc., Somerville, N.J., U.S.A. This material is approved by the U.S. Food and Drug Administration for implantation into the human body. A still further embodiment of the tape 12 is a combination of a synthetic material 11 and a natural material 13 centered between the synthetic material 11 as shown in FIGS. 2b–c. A still further embodiment of the tape 12 includes a combination of synthetic material 11 and natural material 13, whereby the natural material is placed over or incorporated within a generally central portion of the synthetic material 11. One advantage of the tape configurations is that natural material 13 is along the center region of tape 12 so that after installation of tape 12, natural material 13 is positioned below the urethra and eliminates possible erosion issues at the interface of the urethra and tape. Natural material 13 may be connected to the synthetic material 11 by means of sewing, a bio-compatible glue, cell culturing techniques or other known means.

Tape 12 may be of any convenient shape that suits the intended purpose of the invention. An exemplary width is about 1 cm and the length would be dependent upon the size of the female undergoing the procedure. Tape 12 may be single or double ply, generally planar in structure, or tubular (FIG. 2d) to provide additional supporting strength and more surface area on which tissue fibers may attach. Moreover, tape 12 may consist of different types of material, such as a bioabsorbable and non-bioabsorbable material. Tape 12 may also be coated with an antimicrobial additive to prevent or minimize infection and a lubricous coating, for example, a bioabsorbable hydrogel, to facilitate the tape passing through the tissue as discussed below. Preferably, tape 12 is covered by a removal plastic sheath as disclosed in U.S. Pat. No. 5,899,909. The tape may also be made radio-opaque and/or of a contrasting color to the body tissue to allow for future diagnostic visualization.

In one embodiment tape 12 may be attached to needle segment 20 by means of tying, gluing or other suitable attaching means. Preferably, a bio-compatible heat shrink tube fixes tape 12 onto needle portion 20, FIG. 2a. In a further embodiment, as shown in FIGS. 2b–d and 3a–g, needle 10 and tape 12 are further configured to enable easy attachment and detachment of tape 12 to and from needle 10 by the surgeon during the operation. This embodiment allows for the use of a single needle for the procedure. This embodiment also allows for the use of a tape constructed, at least in part, of natural materials, which are otherwise not suitable in the pre-affixed embodiment due to the inability of the natural material to survive extended periods in inventory.

Figure 3A:
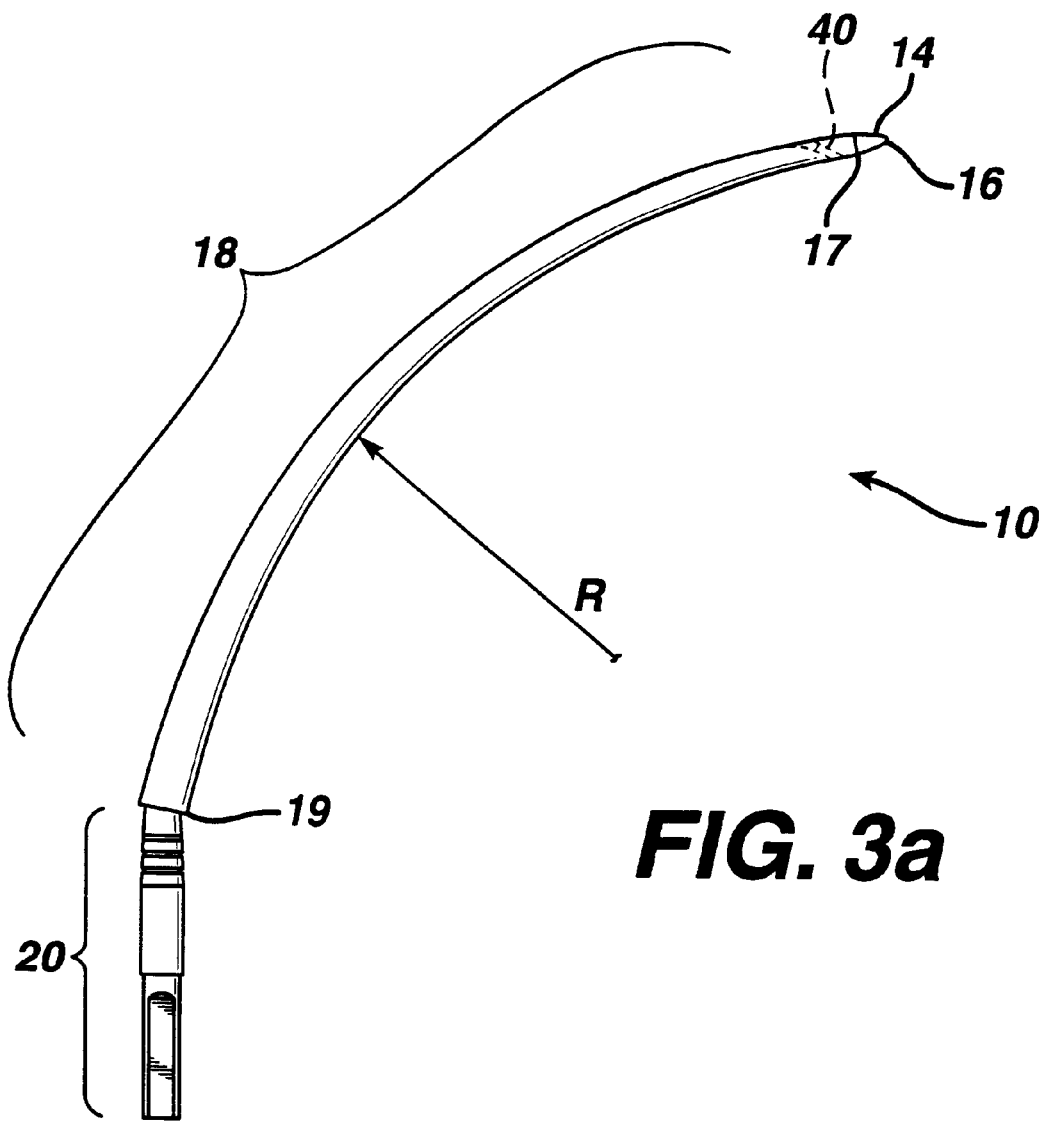
FIG. 3a is a side view of an alternate embodiment of the needle.

In one embodiment, shown in FIGS. 3a–c, shaft 18 provides for a notch or slot 40 to slidably receive connecting tabs 32 and 32a that are attached at either ends of tape 12. Preferably, slot 40 extends through curved shaft 18 and is further located at the distal end 17 of needle 10 so that tape 12 may be disconnected from needle 10 immediately after needle 10 penetrates the abdomen wall, discussed below.

Tab 32 may be constructed from any bio-compatible material, such as plastic or metal. Tab 32 can be any shape, such as a square or arrow shape, so long as tap 32 can be securely inserted into notch or slot 40. FIGS. 3b–c illustrates tab 32 having two spring arms 33 and 33a that when inserted into slot 40 expand and securely fasten tab 32 within slot 40. Tab 32 may be attached to tape 12 in any number of convenient methods as previously discussed and well known to those skilled in the art.

FIGS. 3d–e illustrates a two-tier slot 40, wherein tab 32 slides into the lower tier which holds tab 32 in place. Alternate means of capturing tab 32 within slot 40 are available as is well known in the art.

FIGS. 3f–g illustrate an alternate embodiment of affixing tape 12 to the distal end 17a of needle 10. A detachable blunt tip 16a having a connecting post 15, attaches to the distal end 17a by means of a mounting hole 15a to accept post 15. Post 15 may be securely attached to hole 15a either by compression fit, mating threads or other convenient attachment methods. Distal end 17a further defines a groove 23 of varying depth to allow the end of tape 12 connected to post 15 to transition from within hole 15a to the exterior of needle 10. Along with the embodiment of FIGS. 3a–e, this embodiment allows the surgeon to affix tape 12 to needle 10 just prior to the surgical procedure. One advantage is the ability to use a tape 12 constructed of, at least in part, a natural material.

As would be appreciated by one skilled in the art, there exist multiple means for detachably connecting the tape to the needle. Alternate embodiments would include tying the ends of tape 12 to form a knot and securely inserting the knot into a V-type groove in shaft 18. Alternately, a diagonal slit in shaft 18 could accept tape 12 or a suture extending from tape 12.

The surgical procedure for implanting tape 12 using two needles is shown in FIGS. 4a–g. In the figures the relevant parts of the female lower abdomen are disclosed, the vagina being 50, the uterus 52, the urethra 54, the pubic bone 56, the urinary bladder 58 and the abdominal wall 60. The first needle 10a penetrates the vaginal wall, an incision having first been made in the wall to create a tissue flap. The needle is attached to handle 21, and the surgeon guides needle 10a through the vaginal wall and through the soft tissue on one side of the urethra 54, the needle then according to FIG. 4b being passed close to the back of the pubic bone 56, through additional layers of fat, muscle and fascia, and then through the abdominal wall 60 above the pubic bone 56. An incision can be made through the abdominal wall for the passage of the needle therethrough. Handle 21 is disconnected from needle 10a, FIG. 4c, and the needle 10a along with tape 12 are withdrawn from the abdomen wall by means of forceps, FIG. 4d.

Figure 4A:
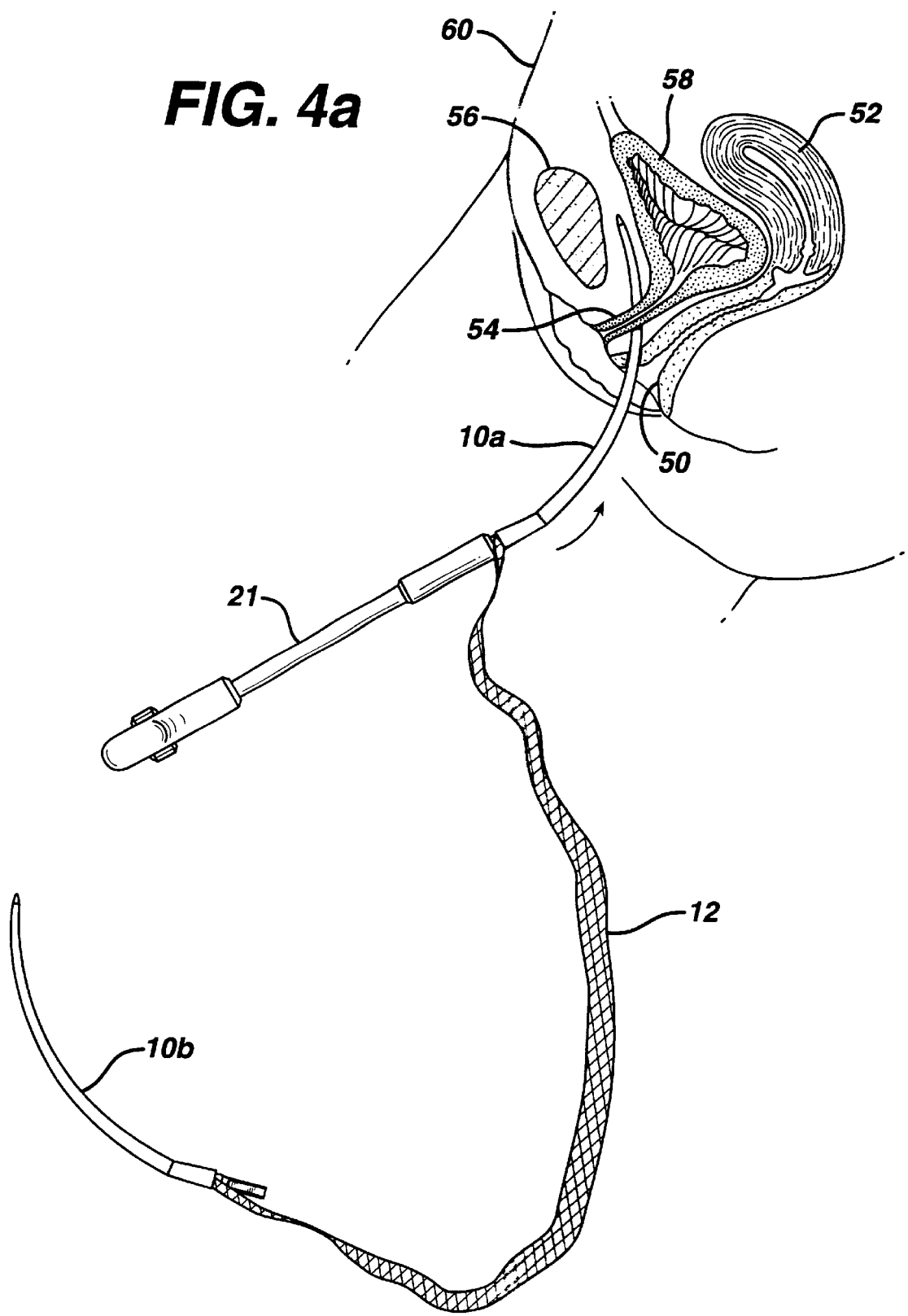
FIGS. 4a–g illustrate diagrammatically several surgical steps of the method utilizing two needles according to the invention to treat SUI.
Figure 4B:
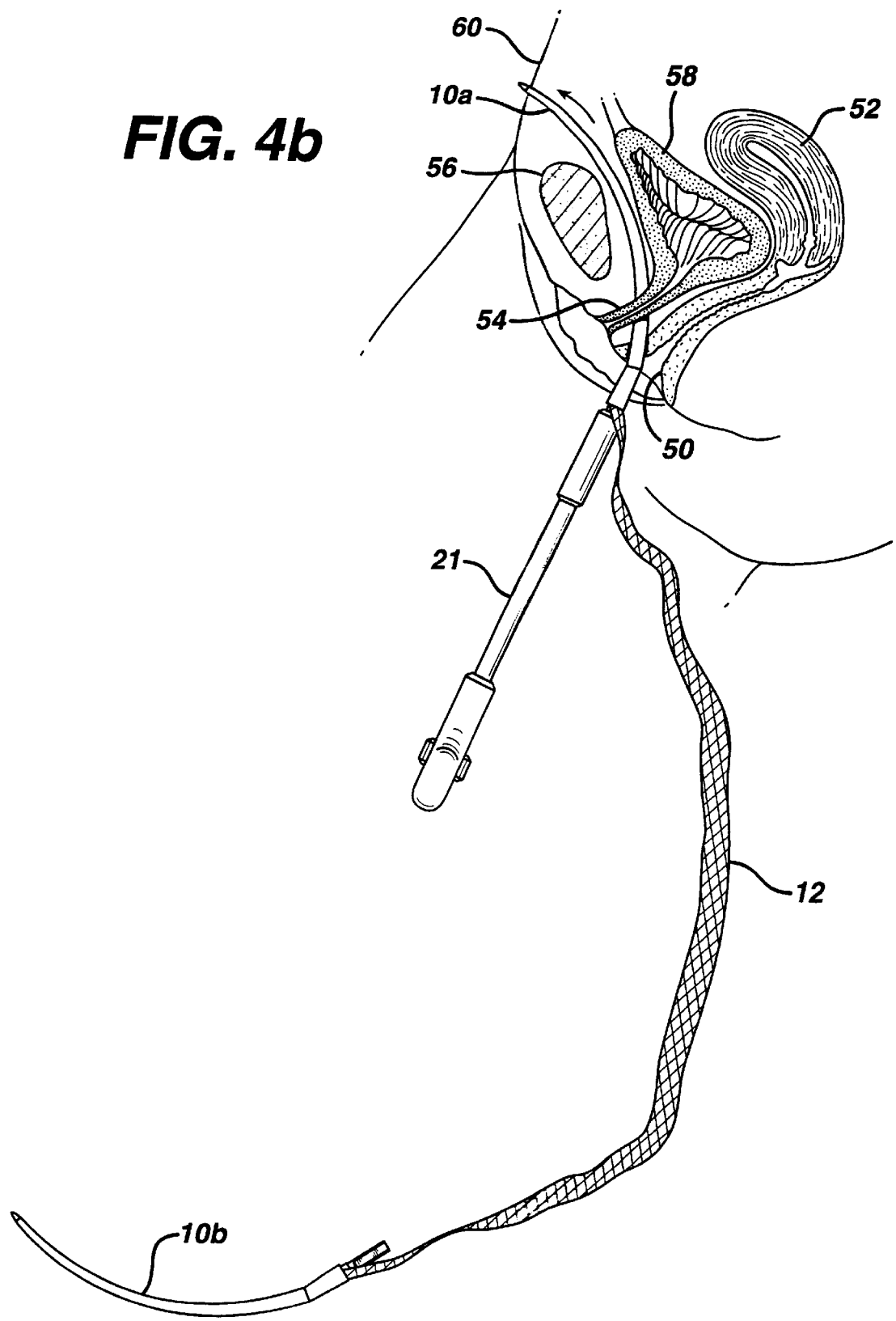
Figure 4C:
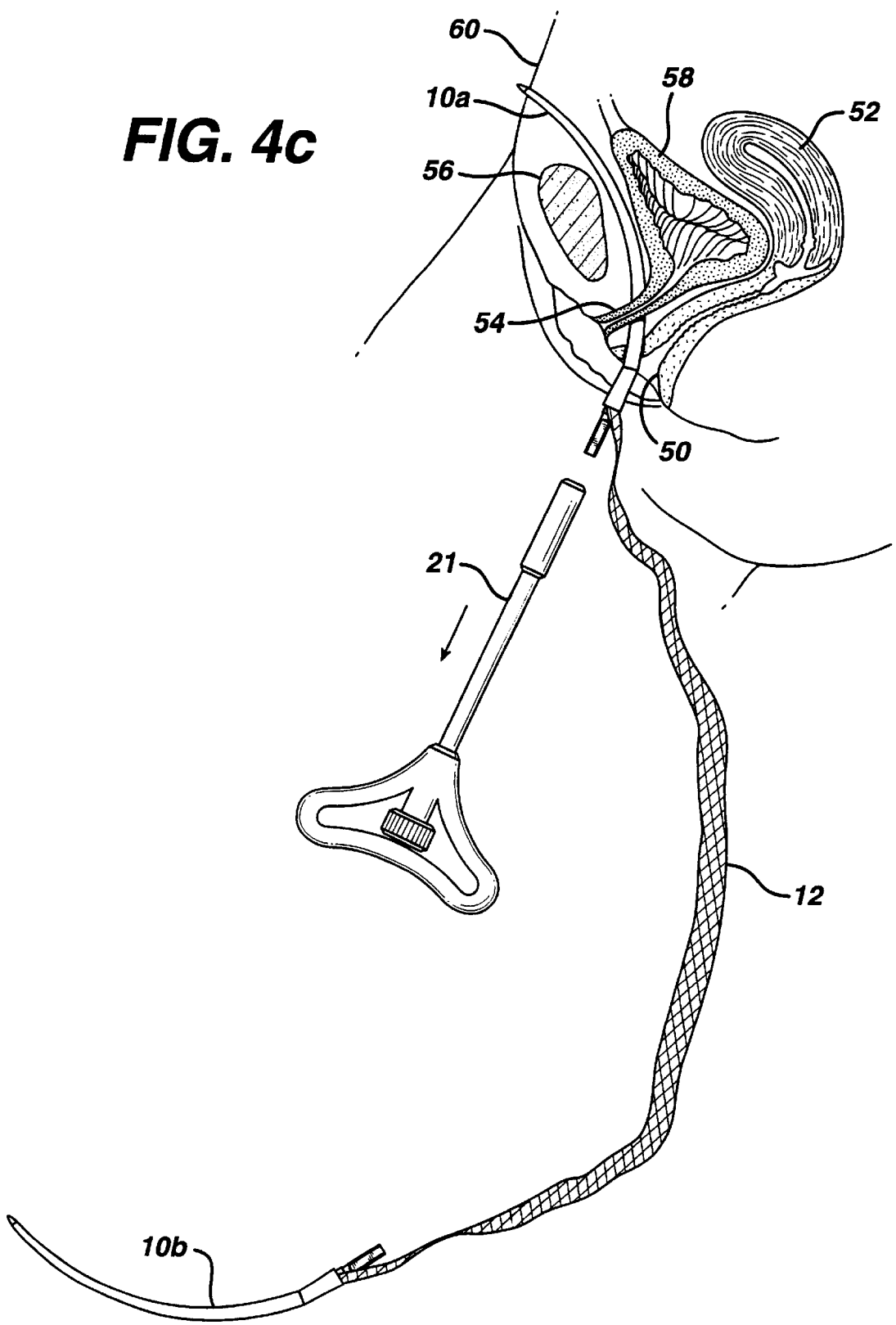
Figure 4D:
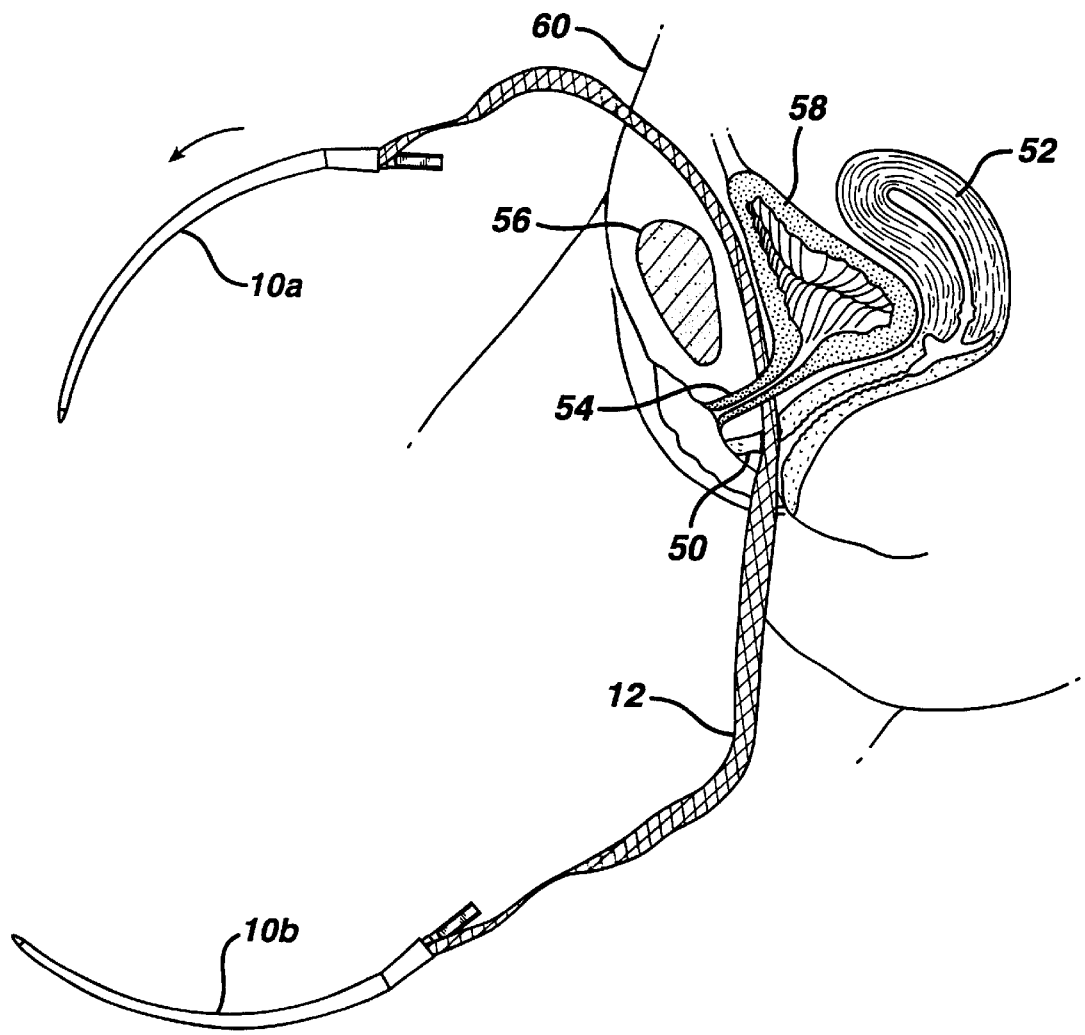
Figure 4E:
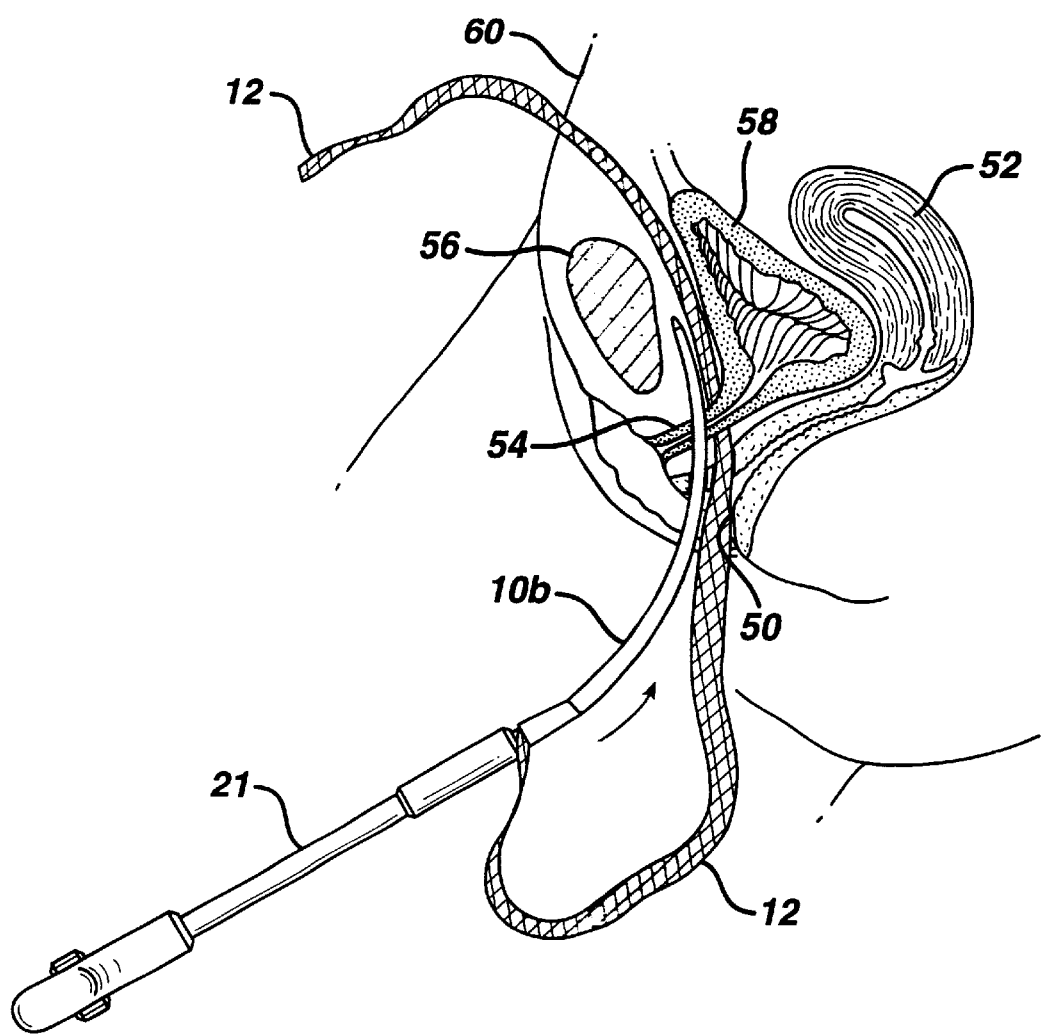
Figure 4F:
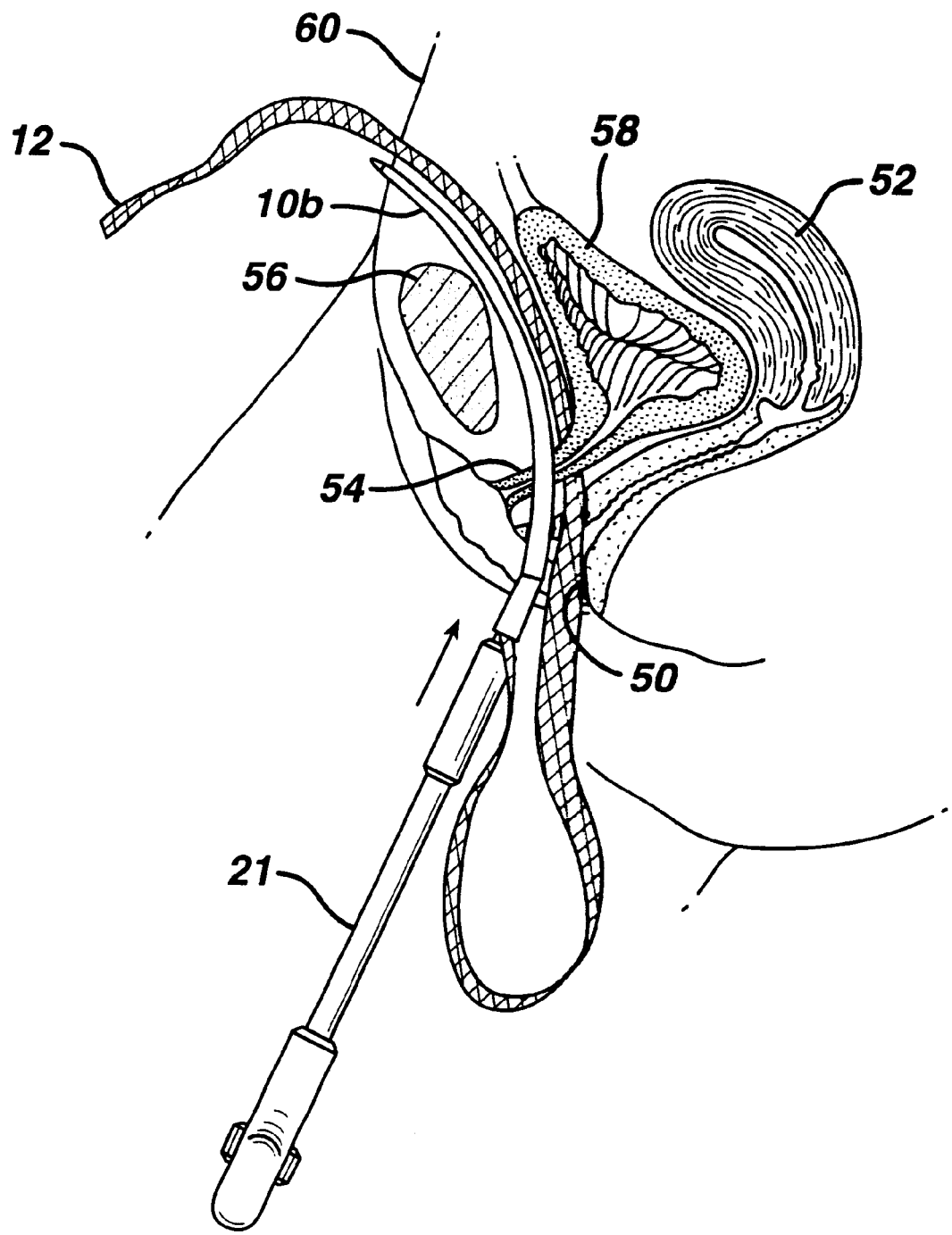
Figure 4G:
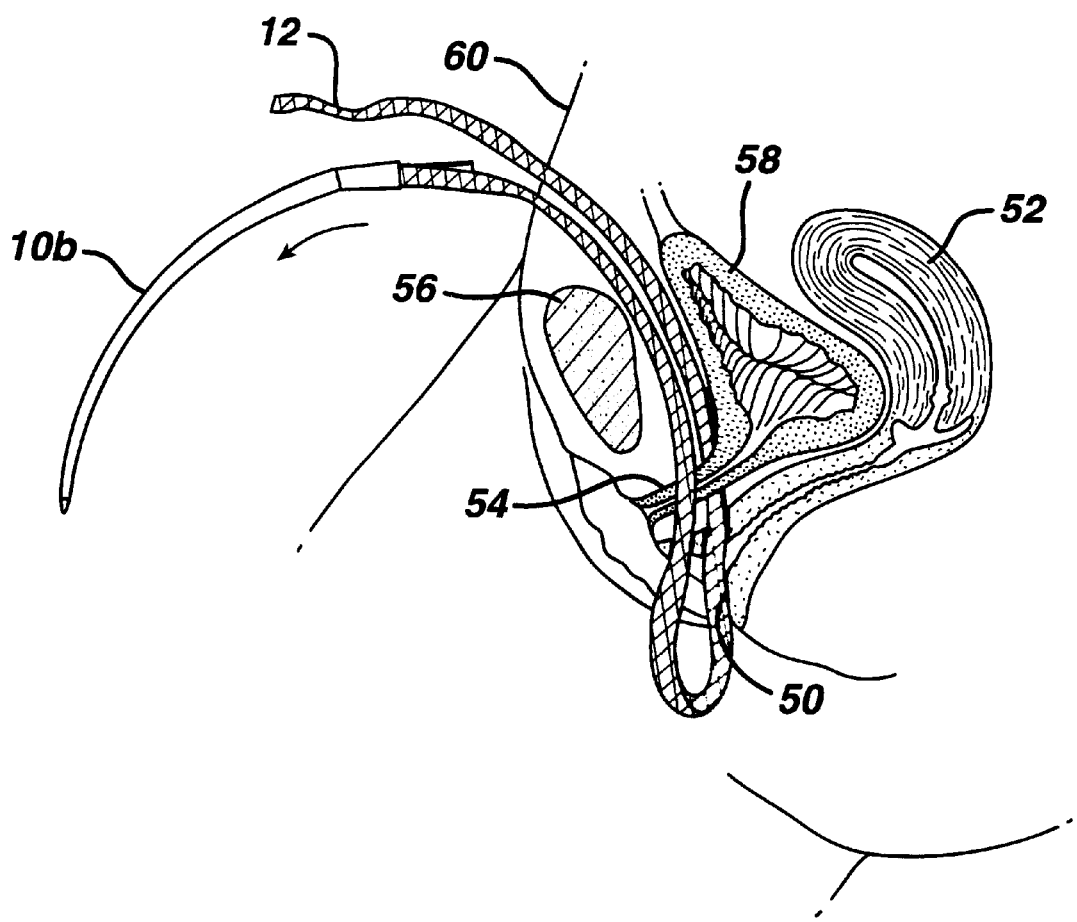

Referring to FIG. 4e, needle 10b is now attached to handle 21, and needle 10b is passed through the incision in the vaginal wall as guided by the surgeon and through the soft tissue on the opposite side of the urethra than the previous end of tape 12. Needle 10b passes close to the back of the pubic bone, through additional layers of fat, muscle and fascia, FIG. 4f, and then through the abdominal wall above the pubic bone and withdrawn, FIG. 4g.

FIGS. 5a–g illustrate an alternate method of implanting tape 12 using a single needle 10. Tape 12 is attached to needle 10 by means of tab 32 (not shown). Needle 10 penetrates the vaginal wall, an incision having first been made in the wall to create a tissue flap. The surgeon guides needle 10 through the vaginal wall and through the soft tissue on one side of the urethra 54, the needle then according to FIG. 5b being passed close to the back of the pubic bone 56, through additional layers of fat, muscle and fascia, and then through the abdominal wall 60 above the pubic bone 56. An incision can be made through the abdominal wall for the passage of the distal end 17 therethrough. Needle 10 only continues to pass through the abdominal wall until tab 32 may be disconnected from shaft 18, FIG. 5c. To do so, the surgeon simply inserts a narrow instrument into slot 40 to force tab 32 out of slot 40 opposite the side in which tab 32 was inserted. Tab 32 may then be cut off and tape 12 may be pulled out of the abdominal wall to allow the surgeon additional length for the procedure. Needle 10 is then removed from the patient along the same path that it entered, but in the opposite direction, FIG. 5d. Alternatively, needle 10 may be disconnected from handle 21 and pulled out through the abdomen wall 60 using forceps as discussed with regard to the two needle procedure.

Figure 5A:
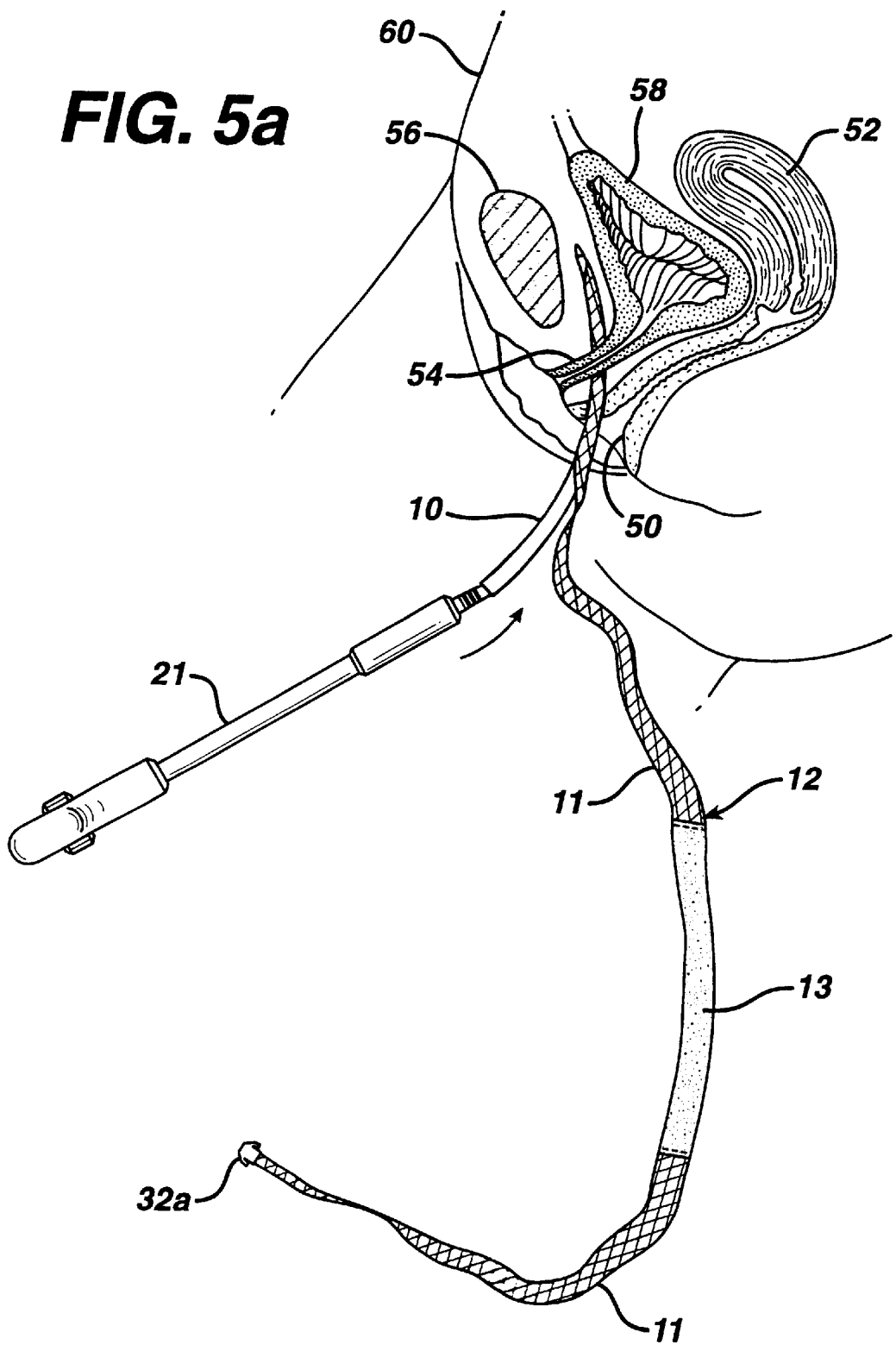
FIGS. 5a–g illustrate diagrammatically surgical steps of the method utilizing one needle according to the invention to treat SUI.
Figure 5B:
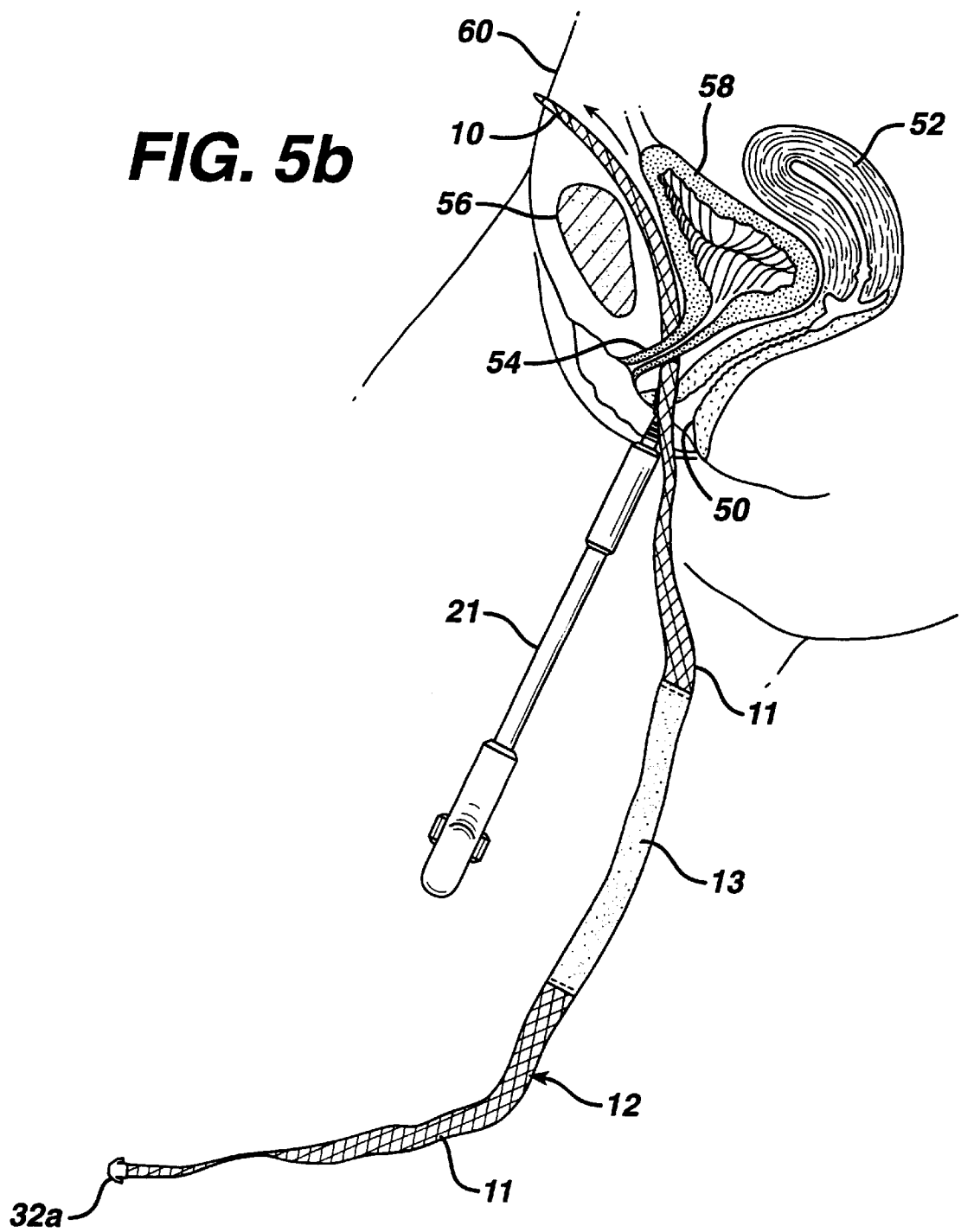
Figure 5C:
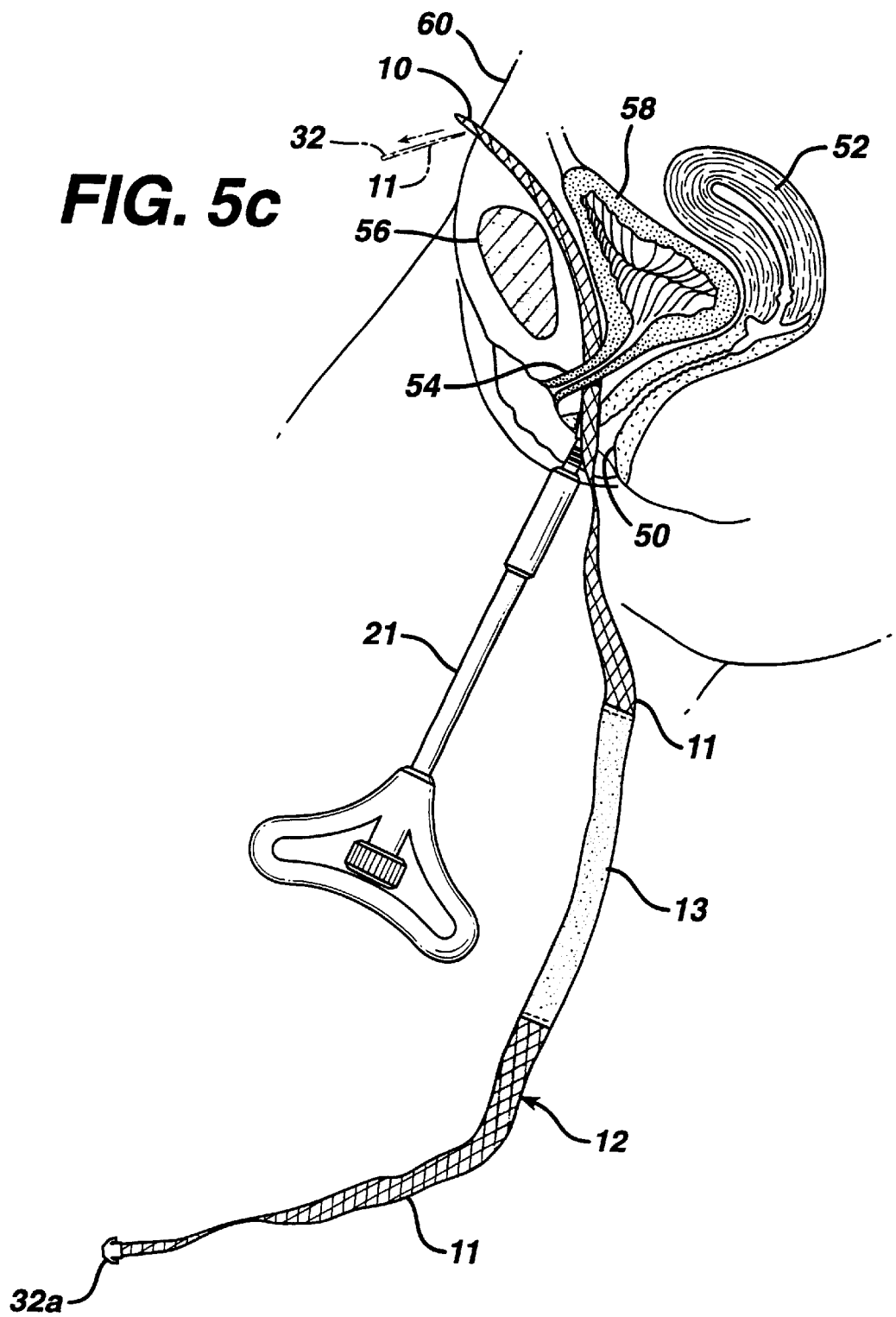
Figure 5D:
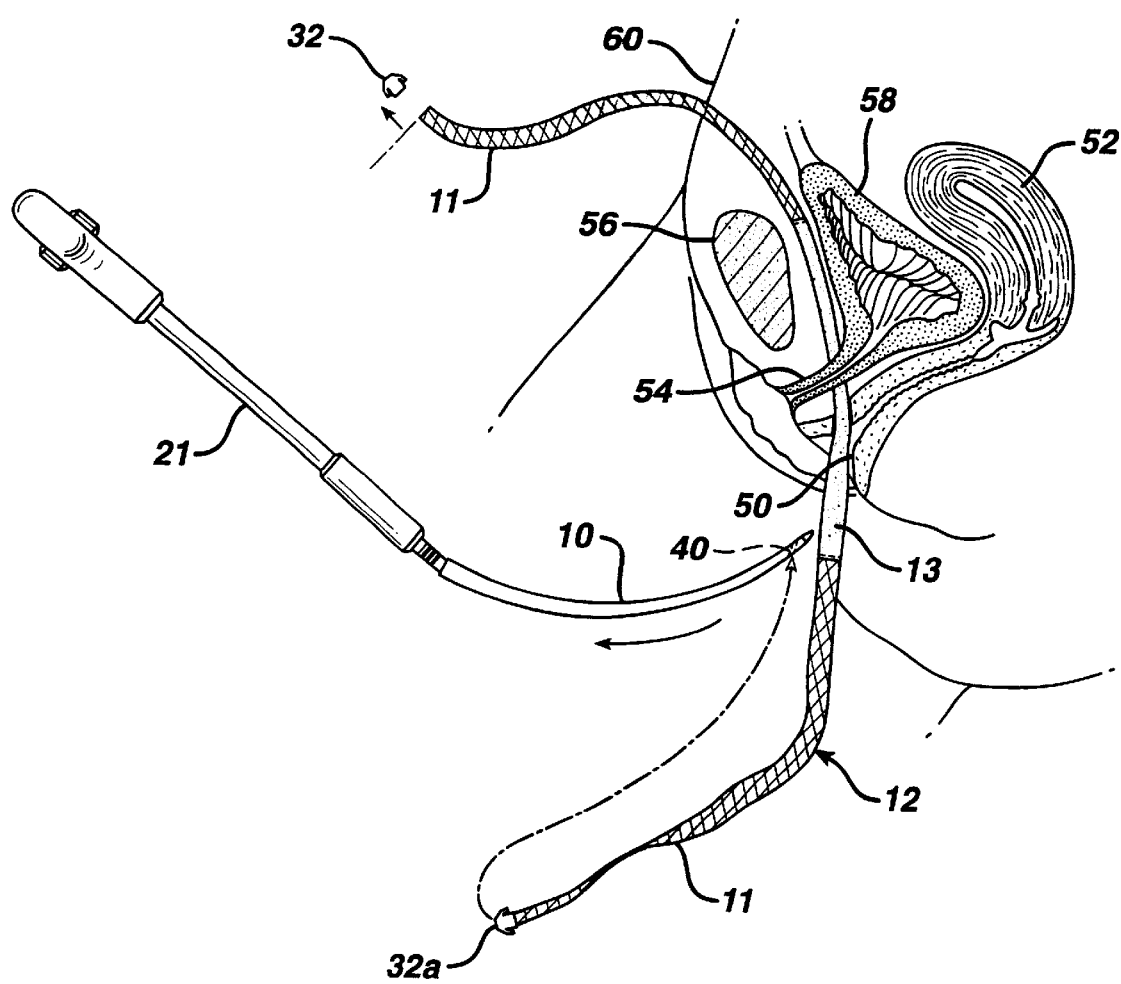
Figure 5E:
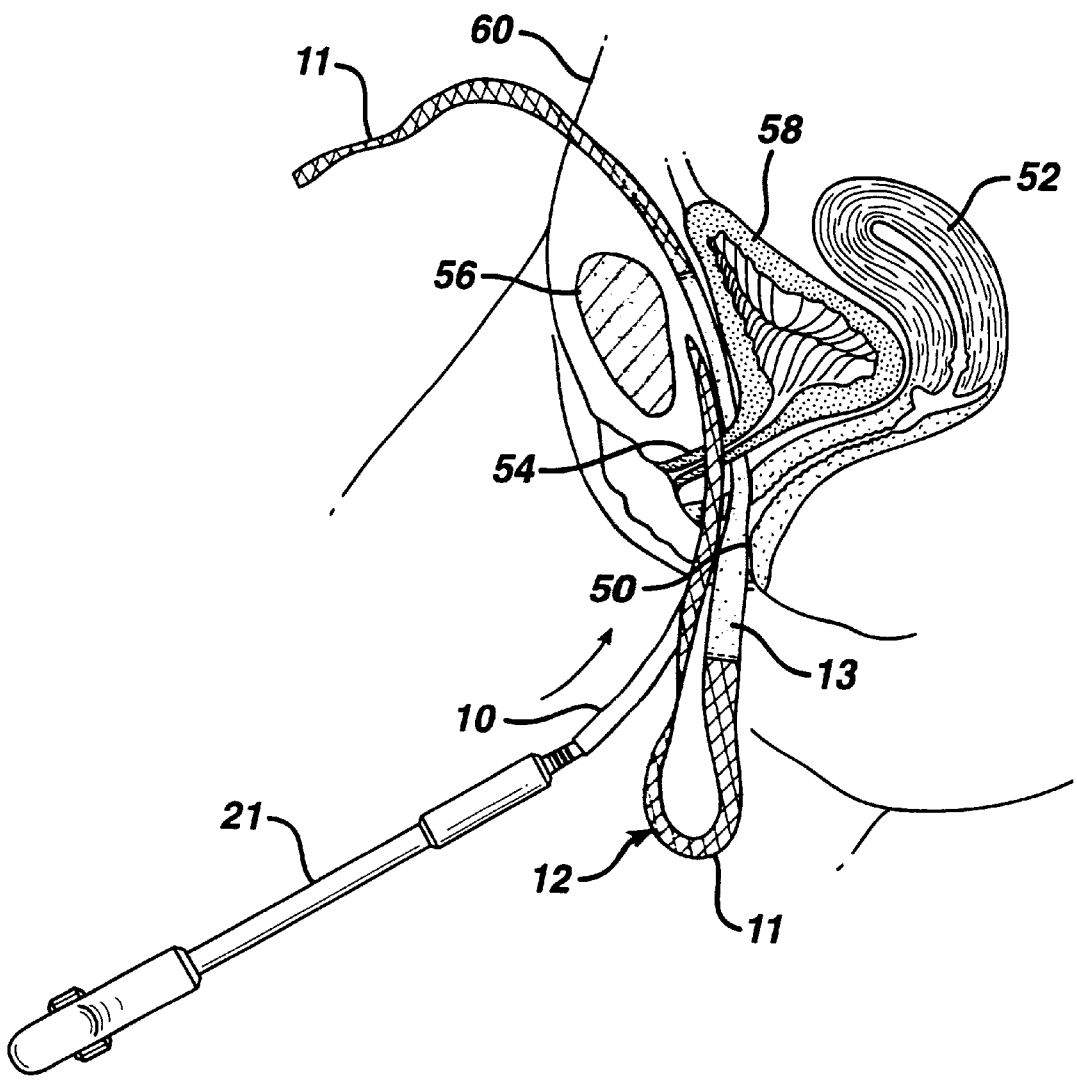
Figure 5F:
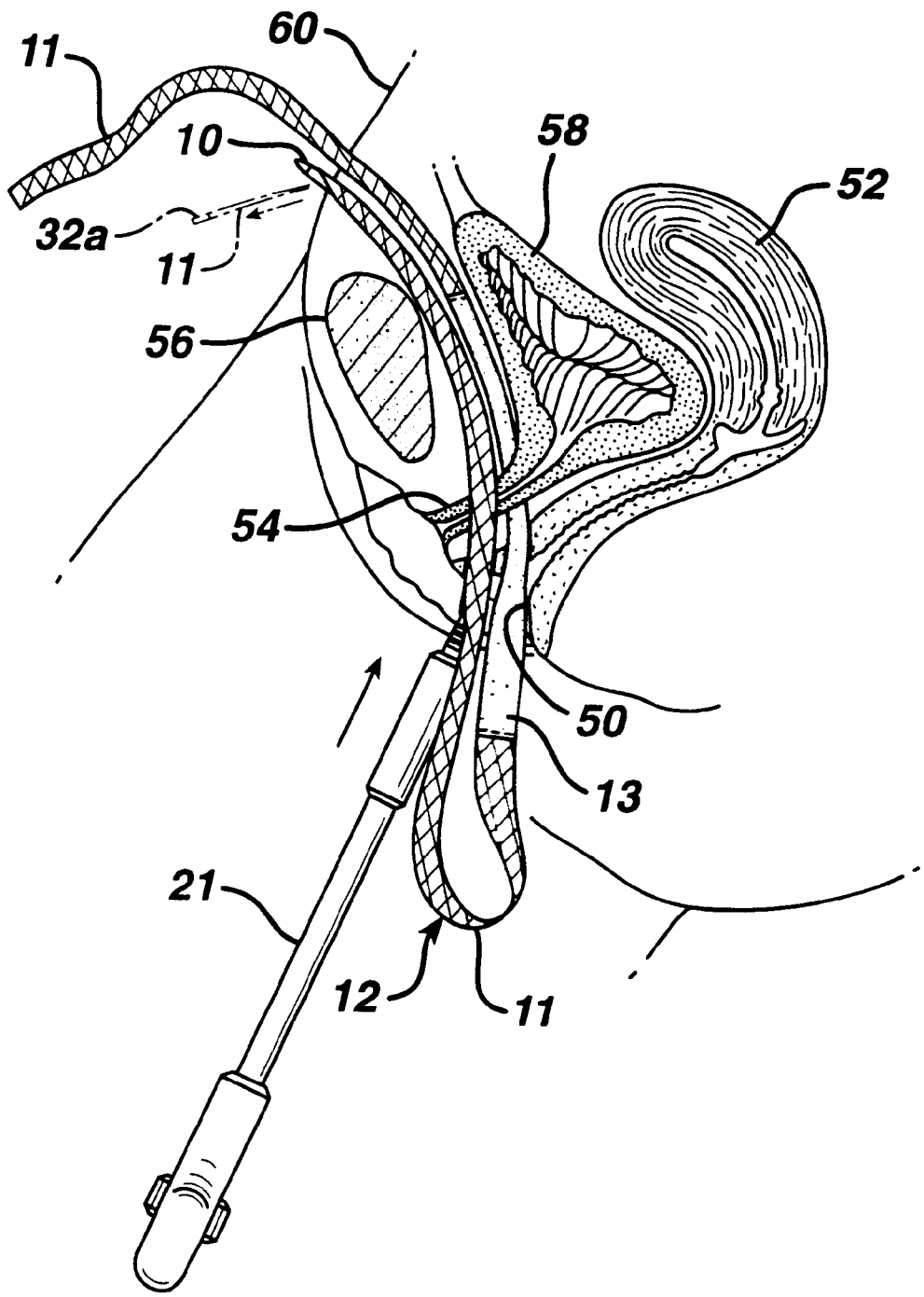
Figure 5G:
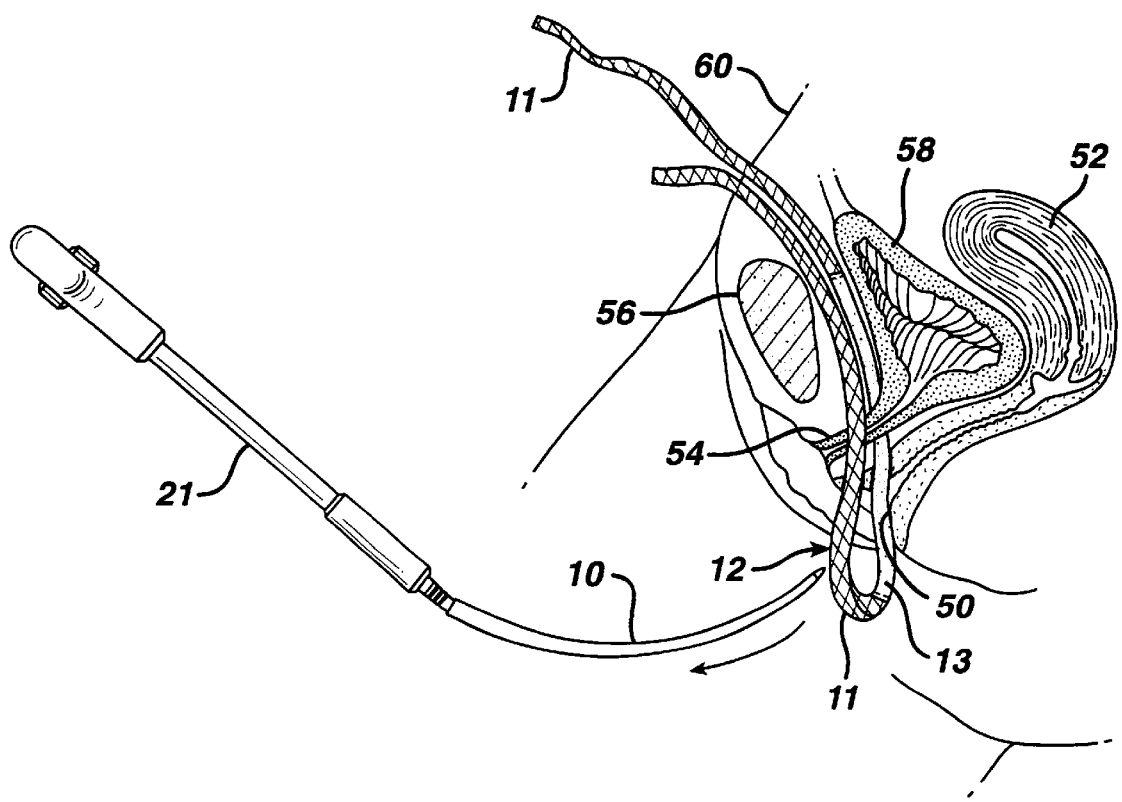

Referring to FIG. 5e, needle 10 is now attached to the opposite end of tape 12 using connector 32a. The surgeon passes needle 10 through the incision in the vaginal wall and through the soft tissue on the opposite side of the urethra than the previous end of tape 12. Needle 10 passes close to the back of the pubic bone, through additional layers of fat, muscle and fascia. FIG. 5f, and then through the abdominal wall above the pubic bone. Needle 10 continues to pass through the abdominal wall only until tab 32a may be disconnected from shaft 18, FIG. 5g. Tape 12 may be pulled out of the abdominal wall to allow the surgeon additional length for the procedure. Needle 10 is then removed from the patient along the same path that it entered, but in the opposite direction. Alternatively, needle 10 may be disconnected from handle 21 and pulled out through the abdomen wall 60 using forceps.

Figure 4H:
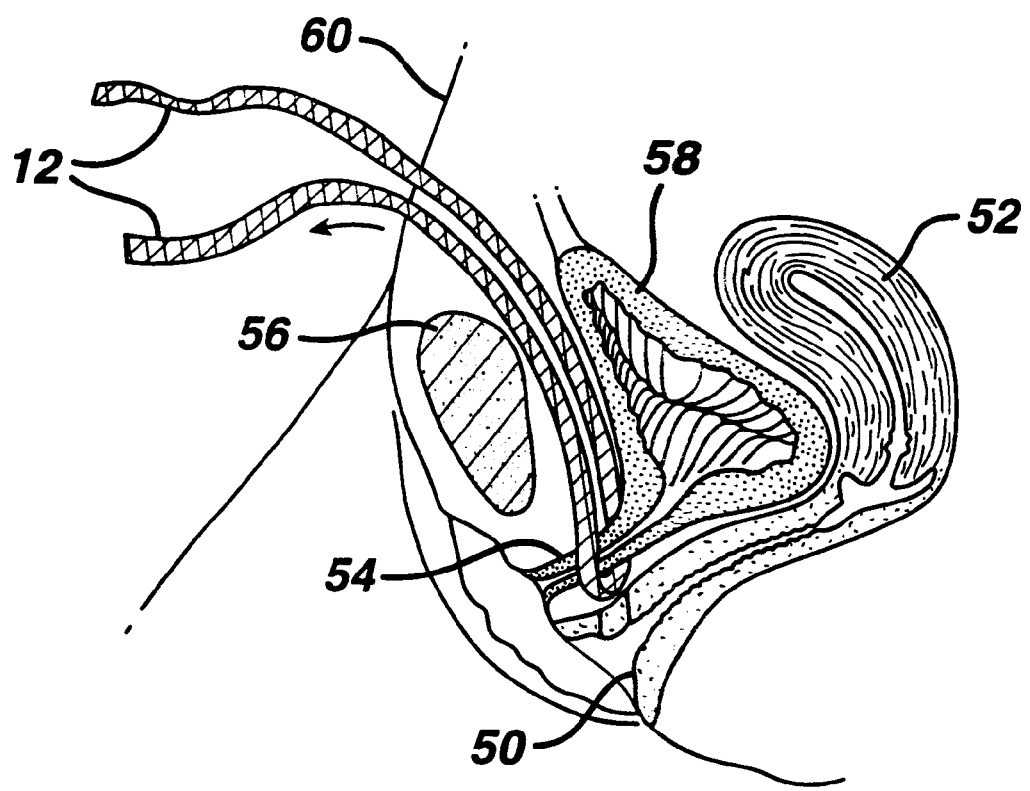
FIG. 4h illustrates the final position of the tape within the body before the tape ends are cut.
Figure 5H:
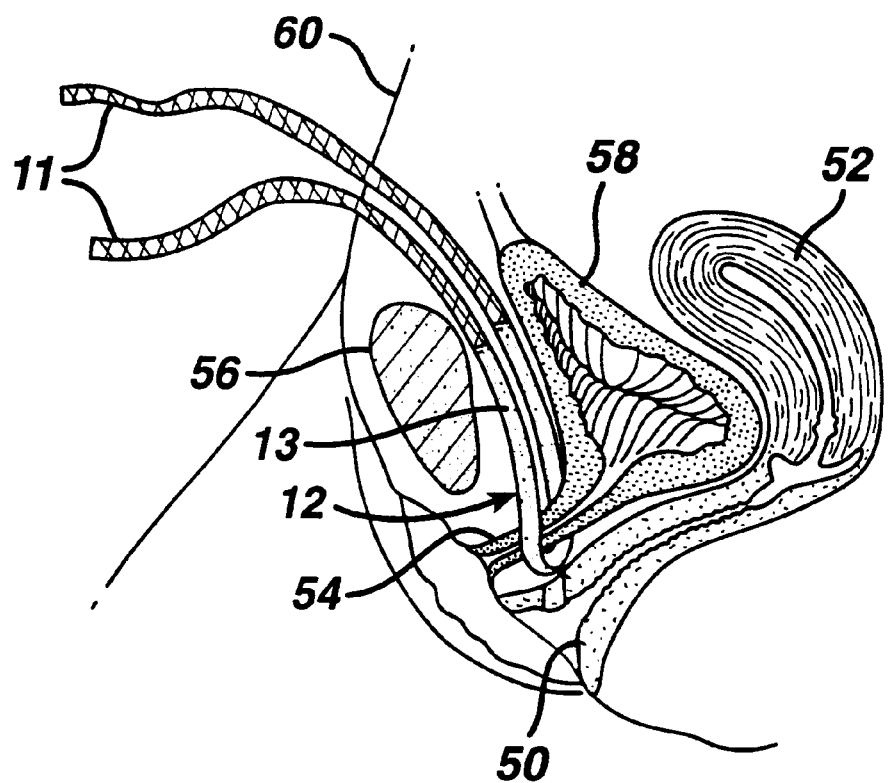
FIG. 5h illustrates the final position of and alternate embodiment of the tape within the body before the tape ends are cut.

Since both procedures may be performed using a local anesthesia, the patient is able to provide feedback to the surgeon after tape 12 is in place. Typically, the urinary bladder 58 is filled with a fluid, such as water, using a catheter and the patient is requested to cough. The surgeon is able to determine the operation of the urethra and may adjust the tension of the tape 12. as necessary, by adjusting the ends of tape 12 located at the outside of the abdomen 60, FIGS. 4h and 5h. After adjustments, the surplus tape at the abdomen is cut off, and the ends of the tape are secured within the abdomen and the abdomen is dosed. Likewise, the incision at the vaginal wall is closed whereby the tissue flap seals the tape between the urethra 54 and the wall of vagina 50.

Tape 12 is left in the body and forms an artificial ligament attached to the abdominal wall that provides the support for the urethra as required in order to restore urinary continence to the patient.

It will be apparent from the foregoing that, while particular forms of the invention have been illustrated and described, various modifications can be made without departing from the spirit and scope of the invention. Accordingly, it is not intended that the invention be limited, except as by the appended claims.

We claim:

1. A surgical instrument for treating female urinary stress incontinence comprising:
   a) a tape for implanting into the lower abdomen of a female to provide support to the urethra; and
   b) a needle element defining in part a curved shaft having a distal end and a proximal end, and a diameter that decreasingly varies from the proximal end to the distal end, and means for attaching to the tape.

2. The surgical instrument of claim 1 wherein the distal end of the needle has a diameter from about 3 mm to about 5 mm.

3. The surgical instrument of claim 1 wherein the proximal end of the needle has a diameter from about 5 mm to about 6 mm.

4. The surgical instrument of claim 1 wherein the tape comprises connecting means and the needle comprises attaching means for detachably accepting the connecting means.

5. The surgical instrument of claim 1 wherein the attaching means is located at the distal end.

6. The surgical instrument of claim 4 wherein the connecting means is a tab element and the attaching means is a slot.

7. The surgical instrument of claim 1 wherein the distal end defines a blunt tip.

8. The surgical instrument of claim 7 wherein the blunt tip has a radius of about 0.6 mm.

9. A surgical instrument for treating female urinary stress incontinence comprising i) a tape for implanting into the lower abdomen of a female to provide support to the urethra, the tape defining a first end and a second end of a synthetic material and the tape further comprising a natural material; and ii). a needle element defining in part a curved shaft having a distal end and a proximal end, and means for attaching to the tape, and a diameter that decreasingly varies from the proximal end to the distal end.

10. The surgical instrument of claim 9 wherein the natural material is selected from the group consisting of autologous, allograft, xenograft and a tissue engineered matrix.

11. The surgical instrument of claim 9 further comprising a curved needle-like element defining in part a curved shaft having a distal end and a proximal end, and means for attaching to the tape.

12. The surgical instrument of claim 11 wherein the curved needle element further defines a diameter that decreasingly varies from the proximal end to the distal end.

13. The surgical instrument of claim 9 wherein the distal end of the needle has a diameter from about 3 mm to about 5 mm.

14. The surgical instrument of claim 9 wherein the distal end of the needle has a diameter from about 5 mm to about 6 mm.

15. The surgical instrument of claim 9 wherein the tape comprises connecting means and the needle comprises attaching means for detachably accepting the attaching means.

16. The surgical instrument of claim 15 wherein the attaching means is located at the distal end.

17. The surgical instrument of claim 15 wherein the connecting means is a tab element and the attaching means is a slot.

18. The surgical instrument of claim 9 wherein the distal end defines a blunt tip.

19. The surgical instrument of claim 18 wherein the blunt tip has a radius of about 0.6 mm.

20. A surgical instrument for treating female urinary stress incontinence comprising:
   a) a tape for implanting into the lower abdomen of a female to provide support to the urethra having connecting means; and
   b) a needle element defining in part a curved shaft having a distal end and a proximal end and attaching means for detachably accepting the connecting means.

21. The surgical instrument of claim 20 wherein the attaching means is located at the distal end.

22. The surgical instrument of claim 20 wherein the connecting means is a tab element and the attaching means is a slot.

23. The surgical instrument of claim 20 wherein the distal end defines a blunt tip.

24. The surgical instrument of claim 23 wherein the blunt tip has a radius of about 0.6 mm.

25. The surgical instrument of claim 20 wherein the curved shaft defines a diameter that decreasingly varies from the proximal end to the distal end.

26. The surgical instrument of claim 25 wherein the distal end of the needle has a diameter from about 3 mm to about 5 mm.

27. The surgical instrument of claim 25 wherein the proximal end of the needle has a diameter from about 5 mm to about 6 mm.

28. A method for treating female urinary incontinence comprising the steps of:
   a) providing a first and second needle element, each defining a curved shaft having a distal end and a proximal end, and a diameter that decreasingly varies from the proximal end to the distal end and a tape attached to both needle elements;
   b) passing the first needle and tape into the body via the vagina and on one side of the urethra and extending the tape over the pubic bone and through the abdomen wall;
   c) passing the second needle and tape into the body via the vagina and on the opposite side of the urethra than the first needle and extending the tape over the pubic bone and through the abdomen wall, creating a supporting sling below the urethra; and
   d) leaving the tape implanted in the body.

29. A method for treating female urinary incontinence comprising the steps of:
   a) providing a needle element defining in part a curved shaft having a distal end and a proximal end and a tape attached thereto; and
   b) passing the needle and tape into the body via the vagina to form a sling around the urethra; and
   c) leaving the tape implanted in the body.

30. A method for treating female urinary incontinence comprising the steps of:
   a) providing a needle element defining in part a curved shaft;
   b) attaching a tape to the needle;
   c) passing the needle and tape into the body;
   d) attaching the tape to the needle and passing the needle and tape into the body to form a sling around the urethra the and
   e) leaving the tape implanted in the body.

\* \* \* \* \*